(12) United States Patent
Heineke et al.

(10) Patent No.: US 6,670,303 B1
(45) Date of Patent: *Dec. 30, 2003

(54) CATALYST HAVING A BIMODAL PORE RADIUS DISTRIBUTION

(75) Inventors: Daniel Heineke, Maikammer (DE); Klaus Harth, Altleiningen (DE); Uwe Stabel, Otterstadt (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/625,485

(22) Filed: Jul. 25, 2000

(30) Foreign Application Priority Data

Aug. 6, 1999 (DE) .......................... 199 37 107

(51) Int. Cl.⁷ .......................... B01J 23/02; B01J 23/04; B01J 23/06; B01J 23/40; B01J 23/58

(52) U.S. Cl. .................... 502/349; 502/242; 502/303; 502/327; 502/328; 502/330; 502/332; 502/334; 502/339; 502/341; 502/344; 502/350; 502/351; 502/352

(58) Field of Search ................. 502/349, 242, 502/102, 238, 239, 258, 261, 262, 303, 327, 328, 332, 330, 334, 339, 350, 351, 352, 341, 344; 501/103, 104, 105, 106, 107, 108, 134, 135; 423/608

(56) References Cited

U.S. PATENT DOCUMENTS

| | | | | |
|---|---|---|---|---|
| 3,670,044 A | * | 6/1972 | Drehman et al. ......... 260/683.3 |
| 3,839,225 A | * | 10/1974 | Acres .......................... 252/432 |
| 3,878,131 A | * | 4/1975 | Hayes ................... 252/466 PT |
| 3,880,776 A | * | 4/1975 | Box, Jr. et al. ........ 252/466 PT |
| 3,898,155 A | | 8/1975 | Wilson ........................ 206/216 |
| 3,960,710 A | | 6/1976 | Pollitzer et al. ............. 208/139 |
| 4,003,852 A | * | 1/1977 | Hayes et al. ............ 252/466 PT |
| 4,008,180 A | * | 2/1977 | Rausch ....................... 252/439 |
| 4,046,715 A | * | 9/1977 | Wilhelm ................. 252/466 B |
| 4,102,822 A | | 7/1978 | Mulaskey ................... 252/465 |
| 4,162,235 A | * | 7/1979 | Acres et al. ................ 252/462 |
| 4,167,496 A | * | 9/1979 | Antos et al. ............. 252/466 B |
| 4,169,815 A | * | 10/1979 | Drehman ............... 252/466 PT |
| 4,366,091 A | * | 12/1982 | Antos ................... 252/466 PT |
| 4,454,026 A | | 6/1984 | Hensley, Jr. et al. ........ 208/251 |
| 4,486,547 A | * | 12/1984 | Imai et al. .................. 502/223 |
| 4,549,957 A | | 10/1985 | Hensley, Jr. et al. ........ 208/216 |
| 4,568,655 A | | 2/1986 | Oleck et al. .................. 502/66 |
| 4,716,143 A | * | 12/1987 | Imai ........................... 502/326 |
| 4,786,625 A | * | 11/1988 | Imai et al. .................. 502/326 |
| 4,788,371 A | | 11/1988 | Imai et al. .................. 585/443 |
| 4,959,338 A | * | 9/1990 | Miura et al. ................. 502/263 |
| 5,009,878 A | | 4/1991 | Scharf ........................ 423/608 |
| 5,220,091 A | | 6/1993 | Brinkmeyer et al. ........ 585/660 |
| 5,221,656 A | | 6/1993 | Clark et al. ................. 502/315 |
| 5,322,821 A | | 6/1994 | Brezny ......................... 501/80 |
| 5,516,741 A | * | 5/1996 | Gascoyne et al. .......... 502/230 |
| 5,593,935 A | * | 1/1997 | Golunski et al. ............ 502/339 |
| 5,902,916 A | | 5/1999 | Rühl et al. .................. 585/266 |
| 5,916,836 A | * | 6/1999 | Toufar et al. ............... 502/326 |
| 5,935,898 A | | 8/1999 | Trübenbach et al. ........ 502/527 |
| 5,958,825 A | * | 9/1999 | Wulff-Doring et al. ..... 502/300 |
| 6,153,547 A | * | 11/2000 | Sterzel ......................... 501/80 |
| 6,162,530 A | * | 12/2000 | Xiao et al. ................ 428/292.1 |

FOREIGN PATENT DOCUMENTS

| | | |
|---|---|---|
| DE | 19500366 | 1/1995 |
| EP | 400 306 | 12/1990 |
| EP | 421 077 | 4/1991 |
| EP | 761 307 | 3/1997 |
| EP | 803 488 | 10/1997 |
| EP | 849224 | 6/1998 |
| WO | 94/29021 | 12/1994 |

* cited by examiner

*Primary Examiner*—Cam N. Nguyen
(74) *Attorney, Agent, or Firm*—Keil & Weinkauf

(57) ABSTRACT

Catalysts having a bimodal pore radius distribution comprise
a) from 10 to 99.9% by weight of zirconium dioxide and
b) from 0 to 60% by weight of aluminum oxide, silicon dioxide and/or titanium dioxide and
c) from 0.1 to 10% by weight of at least one element of main group I or II, an element of transition group III, an element of transition group VIII, of the Periodic Table of the Elements, lanthanum and/or tin, with the proviso that the sum of the percentages by weight is 100.

7 Claims, No Drawings

CATALYST HAVING A BIMODAL PORE RADIUS DISTRIBUTION

BACKGROUND OF THE INVENTION

The present invention relates to catalysts having a bimodal pore radius distribution and comprising a) zirconium dioxide and, if desired, b) aluminum oxide, titanium dioxide and/or silicon oxide and c) at least one element of main group I or II, an element of transition group III, an element of transition group VIII, of the Periodic Table of the Elements, lanthanum and/or tin.

U.S. Pat. No. 5,220,091 discloses catalysts comprising Pt/Sn as active component on a Zn spinel support for the dehydrogenation of small hydrocarbon molecules such as isobutane using steam as diluent. The performance of these catalysts is in need of improvement since, despite the high dilution of the feed with steam (ratio 4:1), only relatively low yields and selectivities are achieved at high reaction temperatures of 600° C. Likewise deserving of improvement is the operating life of the catalysts, since they have to be regenerated after an operating time of only 7 hours.

U.S. Pat. No. 4,788,371 discloses Pt/Sn/Cs/$Al_2O_3$ catalysts for the dehydrogenation of hydrocarbons using steam dilution (e.g. steam/propane=10:1). Despite the high degree of dilution, only low conversions of 21% are achieved.

WO-A-94/29021 discloses catalysts based on mixed oxides of magnesium and aluminum and further comprising a noble metal of group VIII, a metal of group IVa and, if desired, an alkali metal of group Ia, of the Periodic Table of the Elements for the dehydrogenation of, for example, a gas mixture of $H_2O$/propan/$H_2$/$N_2$ in a ratio of 8:7:1:5. A drawback of these catalysts in industrial applications is their low hardness, which makes industrial use difficult. Furthermore, the performance of these catalysts, in particular at low reaction temperatures, is in need of improvement. A further disadvantage is the complicated operating procedure which, to maintain the performance, requires the addition of hydrogen to the feed and the mixing in of nitrogen for further dilution.

BRIEF SUMMARY OF THE INVENTION

It is an object of the present invention to remedy the abovementioned disadvantages.

We have found that this object is achieved by new and improved catalysts having a bimodal pore radius distribution and comprising a) from 10 to 99.9% by weight of zirconium dioxide and b) from 0 to 60% by weight of aluminum oxide, silicon dioxide and/or titanium dioxide and c) from 0.1 to 10% by weight of at least one element of main group I or II, an element of transition group III, an element of transition group VIII, of the Periodic Table of the Elements, lanthanum and/or tin, with the proviso that the sum of the percentages by weight is 100, a process for the dehydrogenation of $C_2$–$C_{16}$-hydrocarbons and the use of these catalysts for this purpose and also a process for producing these catalysts.

DETAILED DESCRIPTION OF THE INVENTION

The catalysts of the present invention comprise, preferably consist of, a) from 10 to 99.9% by weight, preferably from 20 to 98% by weight, particularly preferably from 30 to 95% by weight, of zirconium dioxide of which from 50 to 100% by weight, preferably from 60 to 99% by weight, particularly preferably from 70 to 98% by weight, is in the monoclinic and/or tetragonal modification and b) from 0.1 to 30% by weight, preferably from 0.5 to 25% by weight, particularly preferably from 30 to 20% by weight, of silicon dioxide and c) from 0 to 60% by weight, preferably from 0.1 to 50% by weight, particularly preferably from 1 to 40% by weight, in particular from 5 to 30% by weight, of aluminum oxide, silicon dioxide and/or titanium dioxide in the form of rutile or anatase and d) from 0.1 to 10% by weight, preferably from 0.2 to 8% by weight, particularly preferably from 0.5 to 5% by weight, of at least one element of main group I or II, an element of transition group III, an element of transition group VIII, of the Periodic Table of the Elements, lanthanum and/or tin, where the sum of the percentages by weight is 100.

The amount of a noble metal present in the catalysts of the present invention is generally from 0.01 to 5% by weight, preferably from 0.1 to 1% by weight, particularly preferably from 0.2 to 0.5% by weight.

In the catalysts of the present invention, from 70 to 100%, preferably from 75 to 98%, particularly preferably from 80 to 95%, of the pores are smaller than 20 nm or in the range from 40 to 5000 nm.

To produce the catalysts of the present invention, use can be made of precursors of the oxides of zirconium, titanium, silicon and aluminum (forming the support) which can be converted by calcination into the oxides. These can be prepared by known methods, for example by the sol-gel process, precipitation of the salts, dehydration of the corresponding acids, dry mixing, slurrying or spray drying. For example, a $ZrO_2 \cdot xAl_2O_3 \cdot xSiO_2$ mixed oxide can be prepared by first preparing a water-rich zirconium oxide of the formula $ZrO_2 \cdot xH_2O$ by precipitation of a suitable zirconium-containing precursor. Suitable zirconium precursors are, for example, $Zr(NO_3)_4$, $ZrOCl_2$ or $ZrCl_4$. The precipitation itself is carried out by addition of a base such as NaOH, KOH, $Na_2CO_3$ and $NH_3$ and is described, for example, in EP-A-849 224.

To prepare a $ZrO_2 \cdot xSiO_2$ mixed oxide, the Zr precursor obtained as above can be mixed with an Si-containing precursor. Well suited $SiO_2$ precursors are, for example, water-containing sols of $SiO_2$ such as Ludox™. The two components can be mixed, for example, by simple mechanical mixing or by spray drying in a spray dryer.

When using mixed oxides, it is possible to influence the pore structure in a targeted way. The particle sizes of the various precursors influence the pore structure. Thus, for example, macropores can be generated in the microstructure by use of $Al_2O_3$ having a low loss on ignition and a defined particle size distribution. An aluminum oxide which has been found to be useful for this purpose is Puralox ($Al_2O_3$ having a loss on ignition of about 3%).

To prepare a $ZrO_2 \cdot xSiO_2 \cdot xAl_{2O3}$ mixed oxide, the $SiO_2 \cdot xZrO_2$ powder mixture obtained as described above can be admixed with an Al-containing precursor. This can be carried out, for example, by simple mechanical mixing in a kneader. However, a $ZrO_2 \cdot xSiO_2 \cdot xAl_2O_3$ mixed oxide can also be prepared in a single step by dry mixing of the individual precursors.

Compared to pure $ZrO_2$, the mixed oxides have the advantage, inter alia, that they can be shaped easily. For this purpose, the powder mixture obtained is admixed in a kneader with a concentrated acid and can then be converted into a shaped body, e.g. by means of a ram extruder or a screw extruder.

A further possible way of producing the support having a specific pore radius distribution for the catalysts of the present invention is to add, during the preparation, various polymers which can be partly or completely removed by calcination so as to form pores in defined pore radius ranges. The mixing of the polymers and the oxide precursors can, for example, be carried out by simple mechanical mixing or by spray drying in a spray dryer.

The use of PVP (polyvinylpyrrolidone) has been found to be particularly advantageous for producing the supports having a bimodal pore radius distribution. If PVP is added during a production step to one or more oxide precursors of the elements Zr, Ti, Al or Si, macropores in the range from 200 to 5000 nm are formed after calcination. A further advantage of the use of PVP is that the support can be shaped more readily. Thus, extrudates having good mechanical properties can be produced easily from freshly precipitated water-containing $ZrO_2 \cdot xH_2O$ which has previously been dried at 120° C. when PVP and formic acid are added, even without further oxide precursors.

The mixed oxide supports of the catalysts of the present invention generally have higher BET surface areas after calcination than do pure $ZrO_2$ supports. The BET surface areas of the mixed oxide supports are generally from 40 to 300 $m^2/g$, preferably from 50 to 200 $m^2/g$, particularly preferably from 60 to 150 $m^2/g$. The pore volume of the catalysts of the present invention is usually from 0.1 to 0.8 ml/g, preferably from 0.2 to 0.6 ml/g. The mean pore diameter of the catalysts of the present invention, which can be determined by Hg porosimetry, is from 5 to 20 nm, preferably from 8 to 18 nm. Furthermore, it is advantageous for from 10 to 80% of the pore volume to be made up by pores >40 nm.

The calcination of the mixed oxide supports is advantageously carried out after the application of the active components and is carried out at from 400 to 700° C., preferably from 500 to 650° C., particularly preferably from 560 to 620° C. The calcination temperature should usually be at least as high as the reaction temperature of the dehydrogenation for which the catalysts of the present invention are used.

The catalysts of the present invention have a bimodal pore radius distribution. The pores are mostly in the range up to 20 nm and in the range from 40 to 5000 nm. Based on the pore volume, these pores make up at least 70% of the pores. The proportion of pores less than 20 nm is generally from 20 to 60%, while the proportion of pores in the range from 40 to 5000 nm is generally likewise from 20 to 60%.

The doping of the mixed oxides with a basic compound can be carried out either during their preparation, for example by coprecipitation, or subsequently, for example by impregnation of the mixed oxide with an alkali metal compound or alkaline earth metal compound or a compound of transition group III or a rare earth metal compound. Particularly suitable dopants are K, Cs and lanthanum.

The application of the dehydrogenation-active component, which is usually a metal of transition group VIII, is generally carried out by impregnation with a suitable metal salt precursor which can be converted into the corresponding metal oxide by calcination. As an alternative to impregnation, the dehydrogenation-active component can also be applied by other methods, for example spraying the metal salt precursor onto the support. Suitable metal salt precursors are, for example, the nitrates, acetates and chlorides of the appropriate metals, or complex anions of the metals used. Preference is given to using platinum as $H_2PtCl_6$ or $Pt(NO_3)_2$. Solvents which can be used for the metal salt precursors are water and organic solvents. Particularly suitable solvents are lower alcohols such as methanol and ethanol.

Further suitable precursors when using noble metals as dehydrogenation-active component are the corresponding noble metal sols which can be prepared by one of the known methods, for example by reduction of a metal salt with a reducing agent in the presence of a stabilizer such as PVP. The preparation technique is dealt with comprehensively in the German Patent Application DE-A-195 00 366.

The catalyst can be used as a fixed bed in the reactor or, for example, in the form of a fluidized bed and may have an appropriate shape. Suitable shapes are, for example, granules (crushed material), pellets, monoliths, spheres or extrudates (rods, wagon wheels, stars, rings).

As alkali metal and alkaline earth metal precursors, use is generally made of compounds which can be converted into the corresponding oxides by calcination. Examples of suitable precursors are hydroxides, carbonates, oxalates, acetates or mixed hydroxycarbonates of the alkali metals and alkaline earth metals.

If the mixed oxide support is additionally or exclusively doped with a metal of main group III or transition group III, the starting materials in this case should be compounds which can be converted into the corresponding oxides by calcination. If lanthanum is used, suitable starting compounds are, for example, lanthanum oxide carbonate, $La(OH)_3$, $La_3(CO_3)_2$, $La(NO_3)_3$ or lanthanum compounds containing organic anions, e.g. lanthanum acetate, lanthanum formate or lanthanum oxalate.

The dehydrogenation of propane is generally carried out at reaction temperatures of from 300 to 800° C., preferably from 450 to 700°C., and a pressure of from 0.1 to 100 bar, preferably from 0.1 to 40 bar, and at a WHSV (weight hourly space velocity) of from 0.01 to 100 $h^{-1}$, preferably from 0.1 to 20 $h^{-1}$. Apart from the hydrocarbon to be dehydrogenated, the feed may further comprise diluents such as $CO_2$, $N_2$, noble gases and/or steam, preferably $N_2$ and/or steam, particularly preferably steam.

A specific feature of the catalysts of the present invention is that they are active in the dehydrogenation of hydrocarbons in the presence of steam and it is therefore possible to utilize the advantages associated therewith, for example removal of the equilibrium limitation, reduction in carbon deposits and lengthening of the operating life.

If desired, hydrogen can be added to the hydrocarbon feed, in which case the ratio of hydrogen to hydrocarbon is generally from 0.1:1 to 100:1, preferably from 1:1 to 20:1. The dehydrogenation of hydrocarbons using the catalysts of the present invention is preferably carried out without use of hydrogen.

Apart from the continuous addition of a gas, in particular of steam, it is possible to regenerate the catalyst by passing hydrogen or air over it from time to time. The regeneration itself takes place at from 300 to 900° C., preferably from 400 to 800° C., using a free oxidizing agent, preferably air, or in a reducing atmosphere, preferably hydrogen. Regeneration can be carried out at subatmospheric pressure, atmospheric pressure or superatmospheric pressure. Preference is given to pressures in the range from 0.5 to 100 bar.

Hydrocarbons which can be hydrogenated by means of the catalysts of the present invention are, for example, $C_2$–$C_{16}$-hydrocarbons such as ethane, n-propane, n-butane, iso-butane, n-pentane, iso-pentane, n-hexane, n-heptane, n-octane, n-nonane, n-decane, n-undecane, n-dodecane, n-tridecane, n-tetradecane, n-pentadecane, n-hexadecane, preferably $C_2$–$C_8$-hydrocarbons such as ethane, n-propane, n-butane, iso-butane, n-pentane, iso-pentane, n-hexane, n-heptane, n-octane, particularly preferably $C_2$–$C_4$-hydrocarbons such as ethane, n-propane, n-butane and iso-butane, in particular propane and iso-butane.

Propylene is a sought-after product, particularly for the synthesis of polypropylene or for the synthesis of functionalized monomers and their polymerization products. An alternative to the preparation of propylene by steam cracking of light naptha is the dehydrogenation of propane.

Isobutene is an important product, particularly for the preparation of MTBE (Methyl tert-butyl ether). It is used, particularly in the USA, as a fuel additive for increasing the octane number. Isobutene can be prepared by dehydrogenation of isobutane in a process analogous to that for producing propylene.

EXAMPLES

Catalyst Production

Example 1

A solution of 0.7793 g of $SnCl_2 \cdot 2H_2O$ and 0.5124 g of $H_2PtCl_6 \cdot 6H_2O$ in 400 ml of ethanol was poured over 67.03 g of $ZrO_2 \cdot xSiO_2 \cdot xAl_2O_3$ (MEL, product designation XZO 747/03, 1.6–2 mm granules). The excess solution was removed under a reduced pressure of 28 mbar on a rotary evaporator over a period of 30 minutes. The composition was dried at 100° C. for 15 hours and calcined at 560° C. for 3 hours. A solution of 0.5027 g of $CsNO_3$ and 1.7668 g of $KNO_3$ in 166 ml of water was then poured over the catalyst. The supernatant solution was removed under a reduced pressure of 30 mbar over a period of 30 minutes. The catalyst was dried at 100° C. for 15 hours and calcined at 560° C. for 3 hours.

The catalyst had a BET surface area of 92 $m^2/g$. Mercury porosimetry measurements gave a pore volume of 0.29 ml/g, a pore area of 67 $m^2/g$ and a mean pore radius of 4.9 nm. Based on the pore volume, about 31% of the pores had a diameter of less than 10 nm and about 57% had a diameter in the range from 200 and 4000 nm.

The composition of the catalyst is shown in Table 1.

Example 2

186.73 g of $ZrOCl_2 \cdot 8H_2O$ were dissolved in 800 ml of water. At room temperature, 347 ml of 5 M NaOH were added dropwise to this solution at a rate of 1 ml/min. After a time of about 6 hours, the precipitation was complete and the pH was 14. The precipitated material was aged for 15 hours at 100° C. The suspension was subsequently filtered, the solid was washed with 3000 ml of a 5% strength $NH_4NO_3$ solution and subsequently with pure water until free chloride could no longer be detected. The solid was dried at 100° C. for 16 hours and was then heated at a heating rate of 1° C./min to 600° C. and calcined at this temperature for 12 hours.

110 g of a $ZrO_2$ powder prepared in this way were pretreated with 3.3 g of Walocel in 40 ml of water and the mixture was kneaded for 2 hours, then extruded under a pressure of 30 bar to form 3 mm extrudates and subsequently crushed.

A solution of 0.465 g of $SnCl_2 \cdot 2H_2O$ and 0.306 g of $H_2PtCl_6 \cdot 6H_2O$ in 245 ml of ethanol was poured over 40 g of the crushed material produced as described above (sieve fraction: 1.6–2 mm).

The excess solution was removed under a reduced pressure of 28 mbar on a rotary evaporator over a period of 30 minutes. The composition was dried at 100° C. for 15 hours and calcined at 560° C. for 3 hours. A solution of 0.299 g of $CsNO_3$ and 0.663 g of $KNO_3$ in 105 ml of water was then poured over the catalyst. The supernatant solution was removed under a reduced pressure of 30 mbar over a period of 30 minutes. The catalyst was dried at 100° C. for 15 hours and calcined at 560° C. for 3 hours.

The catalyst had a BET surface area of 107 $m^2/g$. Mercury porosimetry measurements gave a pore volume of 0.46 ml/g, a pore area of 102 $m^2/g$ and a mean pore radius of 7.7 nm. Based on the pore volume, about 37% of the pores had a diameter of not more than 10 nm and about 40% had a diameter in the range from 200 and 5000 nm.

The composition of the catalyst is shown in Table 1.

Example 3

373.46 g of $ZrOCl_2 \cdot 8H_2O$ were dissolved in 3200 ml of water. At room temperature, 694 ml of 5 M NaOH were added dropwise to this solution at a rate of 1 ml/min. After a time of about 6 hours, the precipitation was complete and the pH was 14. The precipitated material was aged for 15 hours at 100° C. The suspension was subsequently filtered, the solid was washed with 6000 ml of a 5% strength $NH_4NO_3$ solution and subsequently with pure water until free Cl⁻ could no longer be detected. The solid was dried at 100° C. for 16 hours. 6 g of PVP (polyvinylpyrrolidone) and 6 g of concentrated formic acid in 70 ml of water were added to 200 g of the precipitated material prepared in this way. The mixture was kneaded for 2 hours and extruded under a pressure of 20 bar to form 3 mm extrudates which were subsequently crushed.

A solution of 0.639 g of SnCl$_2$•xH$_2$O and 0.421 g of H$_2$PtCl$_6$•6H$_2$O in 337 ml of ethanol was poured over 40 g of the crushed material produced as described above (sieve fraction: 1.6–2 mm). The excess solution was removed under a reduced pressure of 28 mbar on a rotary evaporator over a period of 30 minutes. The composition was dried at 100° C. for 15 hours and calcined at 560° C. for 3 hours. A solution of 0.411 g of CsNO$_3$ and 0.725 g of KNO$_3$ in 144 ml of water was then poured over the catalyst. The supernatant solution was removed under a reduced pressure of 30 mbar over a period of 30 minutes. The catalyst was dried at 100° C. for 15 hours and calcined at 560° C. for 3 hours.

The catalyst had a BET surface area of 102 m$^2$/g. Mercury porosimetry measurements gave a pore volume of 0.32 ml/g, a pore area of 101 m$^2$/g and a mean pore radius of 7.8 nm. Based on the pore volume, about 50% of the pores had a diameter of not more than 10 nm and about 25% had a diameter in the range from 200 and 2000 nm.

The composition and the performance of the catalyst are shown in Table 1.

Example 4

A solution of 0.384 g of SnCl$_2$•2H$_2$O and 0.252 g of H$_2$PtCl$_6$•6H$_2$O in 196 ml ethanol was poured over 32 g of a crushed ZrO$_2$•xSiO$_2$ mixed oxide from Norton (#9816590; sieve fraction: 1.6–2 mm).

The excess solution was removed under a reduced pressure of 28 mbar on a rotary evaporator over a period of 30 minutes. The composition was dried at 100° C. for 15 hours and calcined at 560° C. for 3 hours. A solution of 0.247 g of CsNO$_3$, 0.435 g of KNO$_3$ and 3.147 g of La(NO$_3$)$_3$•6H$_2$O in 120 ml of H$_2$O was then poured over the catalyst. The supernatant solution was removed under a reduced pressure of 30 mbar over a period of 30 minutes. The catalyst was dried at 100° C. for 15 hours and calcined at 560° C. for 3 hours.

The catalyst had a BET surface area of 82 m$^2$/g. Mercury porosimetry measurements gave a pore volume of 0.27 ml/g, a pore area of 65 m$^2$/g and a mean pore radius of 11.7 nm. Based on the pore volume, about 58% of the pores had a diameter of not more than 20 nm, about 18% of the pores had a diameter of from 40 to 100 nm and about 30% had a diameter of more than 40 and less than 5000 nm.

The composition of the catalyst is shown in Table 1.

Comparative Example 1 (Comp. 1)

A catalyst was prepared for comparison using the method in WO-A-94/29021, Example 1 (Pt/Sn/Cs/Mg(Al)O).

The composition of the catalyst is shown in Table 1.

Comparative Example 2 (Comp. 2)

The catalyst was produced using a method analogous to Comparative Example 1.

The composition of the catalyst is shown in Table 1.

Catalyst Test 20 ml of a catalyst produced as described above were installed in a tube reactor having an internal diameter of 22 mm. The catalyst was treated with hydrogen at 580° C. for 30 minutes. The catalyst was then exposed to a mixture of 80% of nitrogen and 20% of air (lean air) at the same temperature. After a flushing phase of 15 minutes using pure nitrogen, the catalyst was reduced with hydrogen for 30 minutes. 20 standard l/h of propane (99.5% pure) and H$_2$O in a molar ratio of propane/steam of 1:1 were then passed over the catalyst at a reaction temperature of 580° C. or 610° C. The pressure was 1.5 bar and the GHSV was 1000 h$^{-1}$. The reaction products were determined by gas chromatography.

The results using the catalysts of Examples 1 to 4 and the Comparative Examples are shown in Table 1.

TABLE 1

Performance of the catalysts of Examples 1 to 4 and Comparative Examples 1 and 2 in the dehydrogenation of propane*

| Example No./[° C.] | Pt [%] | Sn [%] | K [%] | Cs [%] | ZrO$_2$ [%] | SiO$_2$ [%] | Al$_2$O$_3$ [%] | Conversion [%] after 1 h | Conversion [%] after 17 h | Selectivity [%] after 1 h | Selectivity [%] after 17 h |
|---|---|---|---|---|---|---|---|---|---|---|---|
| 1/580 | 0.3 | 0.6 | 1.0 | 0.5 | 85.6 | 2.1 | 12.0 | 38 | 36 | 85 | 91 |
| 2/580 | 0.3 | 0.6 | 0.5 | 0.5 | 98.1 | — | — | 41 | 34 | 89 | 85 |
| 3/580 | 0.3 | 0.6 | 1.0 | 0.5 | 97.6 | — | — | 38 | 32 | 92 | 86 |
| 4/610 | 0.3 | 0.6 | 0.5 | 0.5 | 90.8 | 4.5 | — | 49 | 45 | 93 | 95 |
| Comp. 1/580 | 0.3 | 0.3 | — | 0.5 | — | — | — | 33 | 29 | 92 | 95 |
| Comp. 2/610 | 0.3 | 0.6 | — | 0.5 | — | — | — | 47 | 38 | 93 | 93 |

*Test conditions: 20 ml of catalyst, granule size = 1.6–2 mm; 580° C. or 610° C.; propane/H$_2$O = 1:1 (mol/mol); 20 standard l/h of propane; GHSV = 1000 h$^{-1}$; 1.5 bar.
**Comparative catalyst: Pt/Sn/Cs/Mg(Al)O from WO-A-94/29021 Example 1.

We claim:

1. A catalyst having a bimodal pore radius distribution, having a BET surface area of greater than 70 m$^2$/g and comprising
   a) from 10 to 99.9% by weight of zirconium dioxide;
   b) from 0 to 60% by weight of aluminum oxide, silicon dioxide and/or titanium dioxide; and
   C) from 0.1 to 10% by weight of at least one element selected from the group consisting of group I, group II, group III, group VIII, of the Periodic Table of the Elements, lanthanum and tin,
      with the proviso that the sum of the percentages by weight is 100.

2. A catalyst having a bimodal pore radius distribution as claimed in claim 1, wherein from 50 to 100% by weight of the zirconium dioxide is in the monoclinic and/or tetragonal modification.

3. A catalyst having a bimodal pore radius distribution as claimed in claim 1, wherein from 70 to 100% of the pores are smaller than 20 nm or in the range from 40 to 5000 nm.

4. A catalyst having a bimodal pore radius distribution as claimed in claim 1, wherein the pore volume is from 0.25 to 0.5 ml/g.

5. A catalyst having a bimodal pore radius distribution as claimed in claim 1 which contains from 0.1 to 50% by weight of potassium and/or cesium.

6. A catalyst having a bimodal pore radius distribution as claimed in claim 1 which contains from 0.05 to 1% by weight of platinum and from 0.05 to 2% by weight of tin.

7. A catalyst having a bimodal pore radius distribution and consisting essentially of
   a) from 10 to 99.9% by weight of zirconium dioxide;
   b) from 0 to 60% by weight of aluminum oxide, silicon dioxide and/or titanium dioxide; and
   c) from 0.1 to 10% by weight of at least one element selected from the group consisting of group I, group II, group III, group VIII, lanthanum and tin,
   with the proviso that the sum of the percentages by weight is, 100.

* * * * *